(12) United States Patent
Zhang et al.

(10) Patent No.: US 10,988,732 B2
(45) Date of Patent: *Apr. 27, 2021

(54) GRAPHENE OXIDE-BASED POROUS 3D MESH

(71) Applicants: Ying Zhang, Shijiazhuang (CN); Julia Xiaojun Zhao, Grand Forks, ND (US); Diane Darland, Grand Forks, ND (US)

(72) Inventors: Ying Zhang, Shijiazhuang (CN); Julia Xiaojun Zhao, Grand Forks, ND (US); Diane Darland, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/774,921

(22) Filed: Jan. 28, 2020

(65) Prior Publication Data
US 2020/0248135 A1 Aug. 6, 2020

Related U.S. Application Data

(63) Continuation of application No. 15/917,045, filed on Mar. 9, 2018.

(60) Provisional application No. 62/469,367, filed on Mar. 9, 2017.

(51) Int. Cl.
*C12N 5/00* (2006.01)

(52) U.S. Cl.
CPC .......... *C12N 5/0068* (2013.01); *C12N 5/0062* (2013.01); *C12N 2533/40* (2013.01); *C12N 2537/10* (2013.01)

(58) Field of Classification Search
CPC .................. C12N 5/0068; C12N 2537/10
See application file for complete search history.

(56) References Cited

FOREIGN PATENT DOCUMENTS

| CN | 102891335 A | 1/2013 |
|---|---|---|
| CN | 104839210 A | 8/2015 |

OTHER PUBLICATIONS

U.S. Appl. No. 15/917,045 (Year: 2018).*
Singh, "Applications and toxicity of Graphene Family Nanomaterials and their Composites," Nanotechnology, Science and Applications, 2016:9, 15-28, (Year: 2016).
Chiu et al, "Generation of Porous Polyethylene glycol Hyrdogels by Salt Leaching," Tissue Engineering: Part C, vol. 16, N 5. 2010, 905-912 (Year:2010).
S. Levenberg et al., "Differentiation of human embryonic stem cells on three-dimensional polymer scaffolds", from PNAS, Oct. 28, 2003, vol. 100, No. 22, pp. 12741-12746.
S. Levenberg et al., "Engineering vascularized skeletal muscle tissue", from Nature Biotechnology, vol. 23. No. 7, Jul. 2005, pp. 879-884.
T. Zhou et al., "Energy metabolism analysis reveals the mechanism of inhibition of breast cancer cell metastasis by PEG-modified graphene oxide nanosheets", from Biomaterials 35 (2014), pp. 9833-9843.
Z. Xu et al., "Covalent Functionalization of Graphene Oxide with Biocompatible Poly(ethylene glycol) for Delivery of Paclitaxel", from ACS Appl. Mater. Interfaces 2014, 6, pp. 17268-17276.

* cited by examiner

*Primary Examiner* — Ruth A Davis
(74) *Attorney, Agent, or Firm* — Kinney & Lange, P.A.

(57) ABSTRACT

A method of making a porous three-dimensional graphene mesh includes combining a graphene-containing material and a polymer having a plurality of hydroxyl groups in an alcohol solvent to form a mixture, adding a salt to the mixture, heating the mixture to form a gel, and washing the gel with water to remove the salt from the gel, leaving behind stable pores to form a scaffold. A three-dimensional porous graphene mesh includes a graphene-containing material and a polymer. The polymer is crosslinked with the graphene-containing material such that the Young's Modulus of the mesh is at least about 5 GPa.

8 Claims, 11 Drawing Sheets

Specification includes a Sequence Listing.

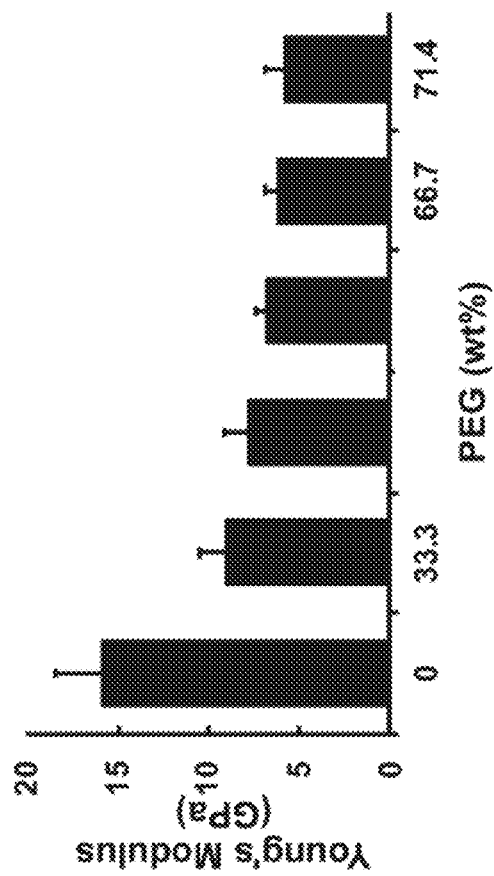
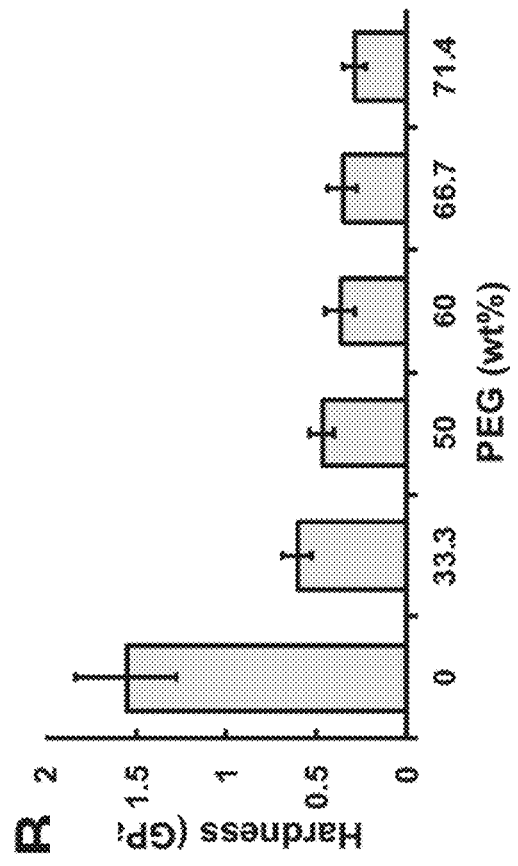
FIG. 2A
FIG. 2B

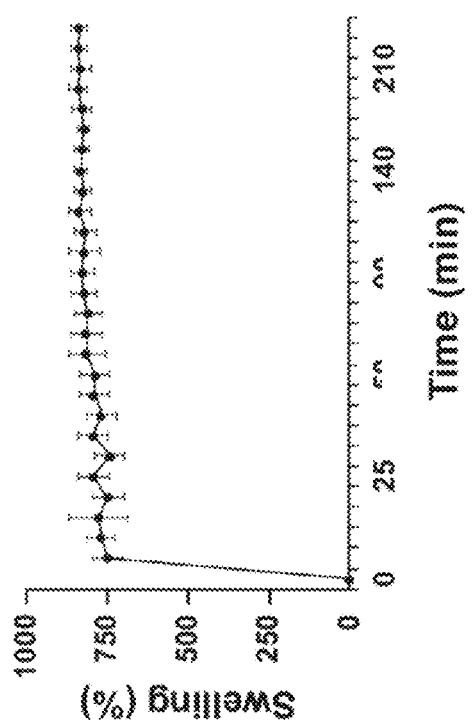
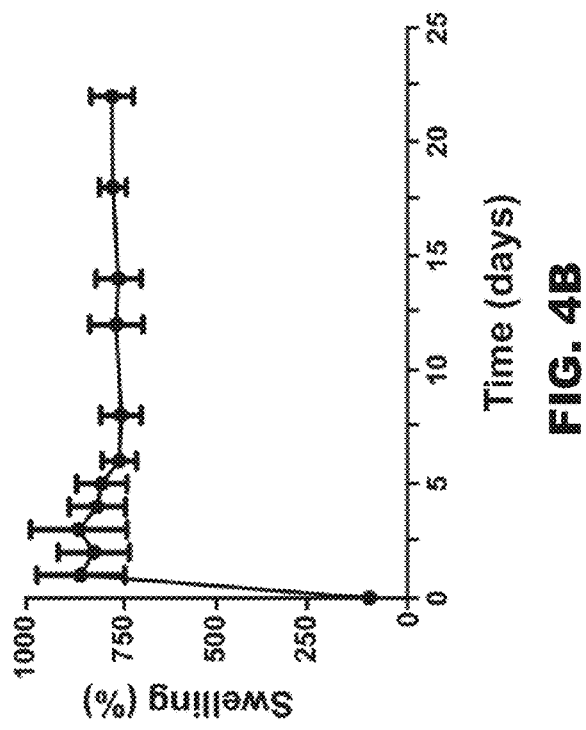
FIG. 4A
FIG. 4B

SEQUENCE LISTING

<160> NUMBER OF SEQ ID NOS: 8

<210> SEQ ID NO 1
<211> LENGTH: 28
<212> TYPE: DNA
<213> ORGANISM: Mus musculus

<400> SEQUENCE: 1
gacacggaca ggattgacag attgatag                                      28

<210> SEQ ID NO 2
<211> LENGTH: 26
<212> TYPE: DNA
<213> ORGANISM: Mus musculus

<400> SEQUENCE: 2
gttagcatgc cagagtctcg ttcgtt                                        26

<210> SEQ ID NO 3
<211> LENGTH: 23
<212> TYPE: DNA
<213> ORGANISM: Mus musculus

<400> SEQUENCE: 3
gtggcaaagt ggagatggtt gcc                                           23

<210> SEQ ID NO 4
<211> LENGTH: 21
<212> TYPE: DNA
<213> ORGANISM: Mus musculus

<400> SEQUENCE: 4
gatgatgacc cgtttggctc c                                             21

```
<210> SEQ ID NO 5
<211> LENGTH: 22
<212> TYPE: DNA
<213> ORGANISM: Mus musculus

<400> SEQUENCE: 5
gatctctcgg aacctcatcg at                                            22

<210> SEQ ID NO 6
<211> LENGTH: 21
<212> TYPE: DNA
<213> ORGANISM: Mus musculus

<400> SEQUENCE: 6
ggcttctttc gcacaatctc a                                             21

<210> SEQ ID NO 7
<211> LENGTH: 20
<212> TYPE: DNA
<213> ORGANISM: Mus musculus

<400> SEQUENCE: 7
ccgagaagag aaaggagcaa                                               20

<210> SEQ ID NO 8
<211> LENGTH: 20
<212> TYPE: DNA
<213> ORGANISM: Mus musculus

<400> SEQUENCE: 8
aaggcaactc caccttctca                                               20
```

GRAPHENE OXIDE-BASED POROUS 3D MESH

CROSS-REFERENCE TO RELATED APPLICATION(S)

This application is a continuation of U.S. application Ser. No. 15/917,045 filed Mar. 9, 2018 for "GRAPHENE OXIDE-BASED POROUS 3D MESH" by Y. Zhang, J. Zhao, and D. Darland, which in turn claims the benefit of U.S. Provisional Application No. 62/469,367 filed Mar. 9, 2017 for "GRAPHENE OXIDE-BASED POROUS 3D MESH" by Y. Zhang, J. Zhao, and D. Darland.

BACKGROUND

One of the major challenges associated with modeling the influence of the cellular microenvironment on cell growth and differentiation is finding suitable substrates for growing the cells in a manner that recapitulates the cell-cell and cell-microenvironmental interactions in vitro.

In recent years, a wide variety of natural materials and synthetic polymers have been recognized/developed as biocompatible materials for effective cultivation of cells that are sensitive to microenvironmental influences, particularly in the field of tissue engineering and high throughput drug testing. The reported natural materials include chitosan, collagen, gelatin, silk fibroin, fibrinogen, elastin, laminin, alginate, hyaluronic acid, and cellulose acetate. The synthetic polymers mainly include poly(l-lactic acid) (PLLA), polycaprolactone (PCL), poly(glycolide) (PGA), poly(lactide-co-glycolide) (PLGA), poly(ethylene oxide) (PEO), poly(vinyl alcohol) (PVA), segmented poly(esterurethane) (SPEU), poly(vinylpyrrolidone) (PVP), and poly(N-isopropylacrylamide) (PNIPAM). While these materials have been adapted for a range of biological applications, drawbacks remain that limit their broad applicability. For example, the surface properties of PGA, PLLA, PLGA, PCL and SPEU are hydrophobic, generating a challenge for cellular applications in tissue engineering. Meanwhile, the surface modification of synthetic polymers and some natural materials can result in poor interactions of cell surface proteins and receptors with modified groups, further complicating cellular interactions with the biomaterial interface. More importantly, it is difficult to keep the 3D structures of these materials stable during the cellular application processes due to the weak mechanical strength of some of these biomaterials, such as PVA, PEO, PVP and collagen. To overcome these limitations, the development of new biocompatible materials is needed.

SUMMARY

A method of making a porous three-dimensional graphene mesh includes combining a graphene-containing material and a polymer having a plurality of hydroxyl groups in an alcohol solvent to form a mixture, adding a salt to the mixture, heating the mixture to form a gel, and washing the gel with water to remove the salt from the gel, leaving behind stable pores to form a scaffold.

A stable three-dimensional material matrix includes a graphene-containing material, a polymer, and salt crystals. The polymer is crosslinked with the graphene-containing material and the salt crystals are integrated with the graphene-containing material and polymer.

A three-dimensional porous graphene mesh includes a graphene-containing material and a polymer. The polymer is crosslinked with the graphene-containing material such that the Young's Modulus of the mesh is at least about 5 GPa.

BRIEF DESCRIPTION OF THE DRAWINGS

FIG. 2A is a graph illustrating the Young's Modulus values for various GO-3D meshes.

FIG. 2B is a graph illustrating hardness values for various GO-3D meshes.

FIGS. 4A and 4B are graphs illustrating swelling properties of a GO-3D mesh.

DETAILED DESCRIPTION

Figure 1:
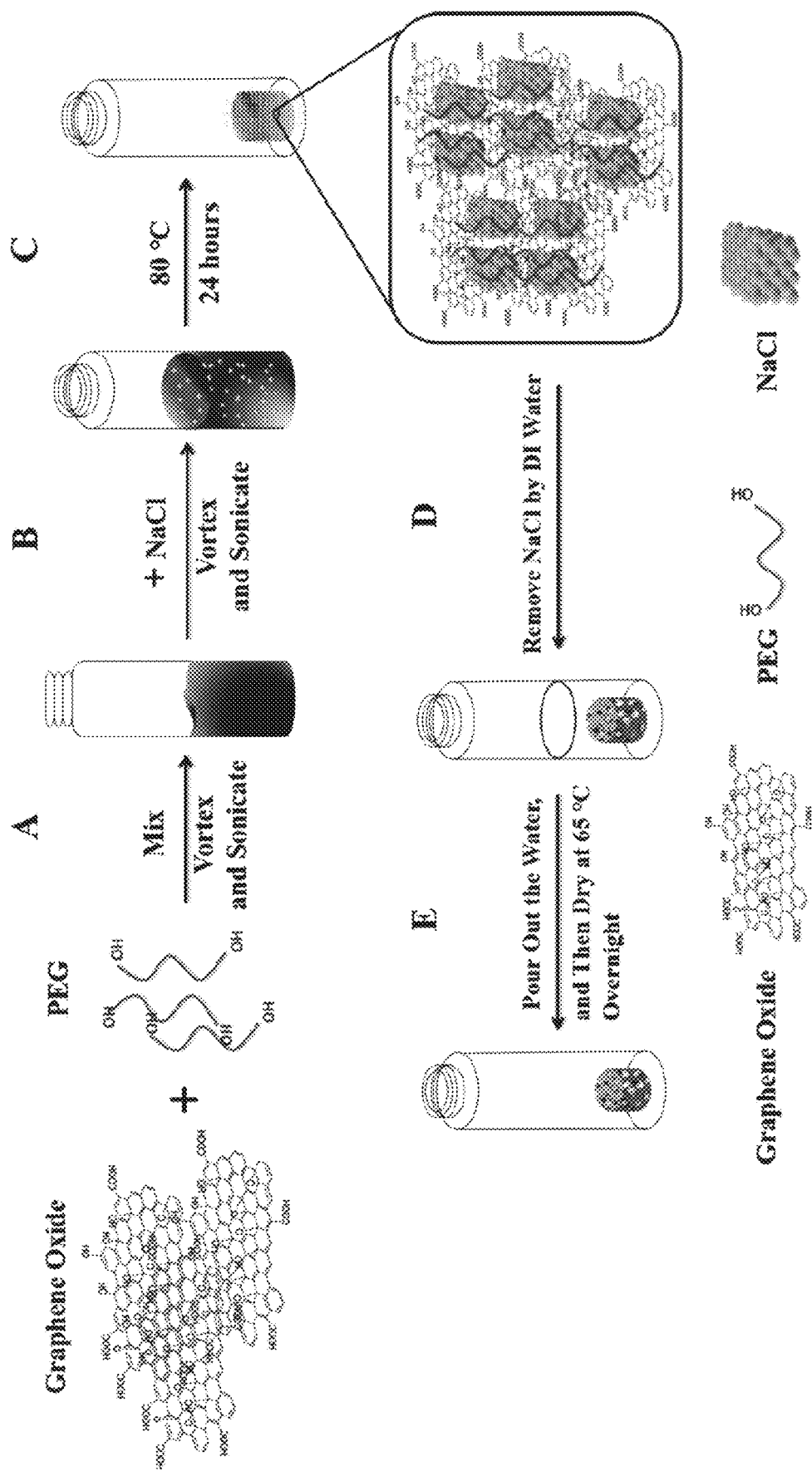
FIG. 1 is a schematic diagram of a method of making a graphene oxide (GO)-polyethylene glycol (PEG) three-dimensional (3D) mesh (GO-3D mesh).

The present disclosure describes graphene oxide (GO) three-dimensional (3D) meshes with tunable hardness and porosity for application in cell culture systems. Methods of preparing GO-3D meshes can be simple, easily reproducible, low cost, and amenable to expanded production. The foundation of the method is the combination of poly(ethylene)(glycol) (PEG) with GO together with a salt leaching approach (NaCl) with a controlled application of heat during the synthetic process to tailor the mechanical properties, porosity and pore size distribution of the resulting GO-3D mesh. With this methodology, the hydrogel formed by PEG and GO generates a microporous mesh in the presence of the NaCl, leading to the formation of a stable 3D scaffold after extensive heating and washing. Scanning electron microscopy was utilized to characterize the morphology and cross section features of the mesh. Varying the ratio of NaCl to GO controls porosity, pore size, and pore connectivity for the GO-3D mesh. When the porosity is less than 90%, with an increasing ratio of NaCl to GO, the number of pores increases with good interconnectivity. A qualitative comparison of the pores on the surface image of the GO-3D mesh with the pores in cross section confirms that the interior pores appear larger and more interconnected in the interior of the mesh. The GO-3D mesh generated with this approach provides an ideal scaffold that can be modified and optimized for a variety of in vitro applications with a range of cell types.

Graphene-based nanomaterials are an emerging field, with graphene being used in a variety of applications ranging from 2D in vitro cell culture, to anticorrosive coatings, or as anchoring structures for calcium carbonate. The cell culture applications for graphene have shown great potential due to several features: (1) tunable mechanical properties by combining graphene and polymers and adjusting their ratio; (2) an available hydrophilic and chemically functional surface for easy cell attachment, proliferation and differentiation; (3) tunable porosity for culturing a variety of cell types; and (4) superior electrical conductivity providing an electrically-compatible surface for cells, the latter feature being critical for establishing a conductive microenvironment for a variety of cell functions. Current graphene materials include graphene, graphene oxides (GOs), and reduced graphene oxides (RGOs). Their mechanical properties are significant. For example, graphene's Young's modulus, a measurement of the stiffness of a solid material, is about 1.02±0.03 TPa with a Poisson's ratio of 0.167, reflecting the elastic potential of graphene-based structures.

The combination of graphene-based materials with polymers further improves the resulting material's properties. The combination of graphene-based materials with chitosan, collagen, and some other polymers has shown improved properties for adhesion and differentiation of neural stem cells. The combination of graphene with a polymer composite structure, such as PLGA-collagen, has been developed for culturing human mesenchymal stem cells and neural stem cells. Recently, PEG was used to modify graphene and graphene oxide nanosheets to improve biodistribution, aqueous stability and biocompatibility. Therefore, while the incorporation of graphene with a polymer provides improved properties, the disadvantage of composite structures generated to date is the lack of tensile strength required to maintain a 3D structure, hydrogen bond linkage, variable stability, and consequent biotoxicity. For example, a tensility analysis for a mixture of graphene/poly(vinyl alcohol) composite revealed that increasing the graphene volume content effectively enhanced the composite's mechanical properties, with the result that the Young's modulus of the graphene-polymer composite (graphene wt %=1.8%) was increased by 150% relative to the polymer alone.

In order to address the challenge of developing a strong, tunable 3D mesh biomaterial, the inventors have taken advantage of the properties of graphene and PEG. PEG is a well-known biocompatible material that is an oligomer of ethylene oxide and presents with several different molecular weights, such as 400 daltons (Da), 1000 Da, 6000 Da and 8000 Da. It is believed that PEG readily forms a hydrogel through the crosslinking of the PEG hydroxyl groups to carboxyl groups of other compounds via a stable hydrogen bond. This linkage property of PEG is used to crosslink the oligomer with GO to form a complex hydrogel. In addition, a salt leaching method (sodium chloride, NaCl) is used to introduce and frame a microporous structure generating a GO-PEG 3D mesh (referred to hereinafter as "GO-3D mesh"). Therefore, the use of PEG to facilitate GO-3D mesh formation and the incorporation of the salt leaching method generate a 3D mesh having stable porosity. Without one or the other (a polymer with suitable hydroxyl groups for crosslinking (e.g., PEG) or the salt leaching step), a suitable (and tunable) GO-3D mesh will not form.

To optimize the scaffold structure and composition, PEG oligomers having different molecule weights can be combined to vary the ratio of PEG to GO to adjust tensility. Moreover, the concentration/amount of NaCl can be varied to control porosity and pore size of the GO-3D mesh. The hydrogel formed by PEG and GO generates a microporous mesh in the presence of the NaCl that is a stable 3D structure after extensive heating and washing. The GO-3D mesh generated provides an ideal scaffold that can be modified and optimized for a variety of in vitro applications with a range of cells types.

The objective of the methods disclosed herein is to develop a biocompatible GO-3D mesh with a tunable porosity and tensility for use in cell culture. One embodiment of a 3D mesh synthesis process is schematically demonstrated in FIG. 1. First, GO and polyethylene glycol (PEG 6000) are mixed in an alcohol to form a GO-PEG gel (FIG. 1, step A). While one specific example is shown, different ratios of GO:PEG were tested. Suitable alcohols include methanol, ethanol, propanol, butanol, pentanol, etc. The alcohol solvent produces a different hydrogel than if water is the solvent. In some embodiments, the GO is a commercially available dispersion of single layer GO film in ethanol. In other embodiments, GO in film form is dispersed in alcohol prior to the addition of PEG or at the same time as the PEG. The GO and PEG form a crosslinked scaffold matrix. The addition of a salt (e.g., sodium chloride (NaCl)) to the GO-PEG gel (FIG. 1, step B) is important for forming a porous 3D structure. The NaCl will establish and maintain a crystalline shape in the GO:PEG mixture when it transitions from liquid to hydrogel solid. With the application of sustained heat (e.g., 80° C. for 24 hours), all of the components, including the GO, PEG6000, and NaCl, become fully integrated (FIG. 1, step C). Enough NaCl is added to form a saturated or supersaturated solution in the GO/PEG/alcohol mixture. Due to the NaCl concentration and the dehydration associated with the heating process, the NaCl crystals form within the GO:PEG matrix. Heat energy is applied so that the mixture is kept between 60° C. and 85° C. The time period for heating and maintaining an elevated temperature can extend between 1 hour and 36 hours. It is expected that more complete crosslinking occurs as the time period increases. As the mixture cools, some of the NaCl forms supercrystals, around which the crosslinked GO and PEG form pores. The next step is to remove the NaCl crystals from the GO-3D mesh with repetitive distilled water flushing (FIG. 1, step D) to yield a 3D mesh scaffold with stable pores left behind. A final step is to dry the porous scaffold overnight to stabilize the 3D mesh obtained (FIG. 1, step E). The drying step can be completed at a temperature between about 40° C. and about 70° C. for a period of time between about 1 hour and about 24 hours. Compared to other methods of preparing graphene 3D structure, such as chemical vapor deposition of GO coating on nickel foams, this method is simpler and has low toxicity during the preparation process.

While the examples described herein describe 3D meshes containing graphene oxide (GO) and polyethylene glycol (PEG) in particular, it is expected that other graphene-containing materials (e.g., graphene, reduced graphene oxides) and other polymers having a sufficient number of hydroxyl groups (whether terminal or not) suitable for hydrogen bonding the graphene-containing materials would also work to synthesize mesh structures. Additionally, while the examples also describe using ethanol in the initial stages of the process to form the 3D mesh, it is expected that other alcohols (e.g., methanol, propanol, etc.) would also work.

EXAMPLES

Synthesis of a GO-3D Mesh

Graphene oxide (GO) dispersed in ethanol (single layer GO dispersion in ethanol, 5 mg/mL, available from ACS materials, Pasadena, Calif.) and PEG 6000 (Sigma-Aldrich, St. Louis, Mo.) were used to generate a GO-3D mesh.

Briefly, a 7.5 mg aliquot of GO was mixed with 15 mg of PEG (MW=6,000 g/mol). The mixture was vortexed for 1 minute followed by sonication for 20 minutes (FIG. 1, step A). Post-sonication, 60 mg of sodium chloride (NaCl) was added to the mixture (FIG. 1, step B), which was subsequently heated to 80° C. for 24 hours to fully integrate the components (FIG. 1, step C). Next, the coalesced mixture was washed to remove NaCl from the porous graphene mesh that had formed (FIG. 1, step D). In the final step to stabilize the 3D structure obtained, the mesh was dried overnight at 65° C. (FIG. 1, step E). Prior to use in cell culture, the mesh was sterilized with ultraviolet light exposure in a cell culture hood for 30 minutes on each side, within 8 inches of a light source that emits standard germicidal high intensity radiation concentrated around 250 nm.

Nanomechanical Property Measurement

Nanomechanical properties of the produced 3D mesh were measured using a nano-indentation device (TI700Ubi) (Hysitron Triboscope, Minneapolis, Minn.) equipped with a Berkovich diamond indenter. Two physical coefficients, hardness and Young's modulus, were assessed to characterize the mechanical properties of the mesh and determine variations associated with changing a single variable—the percentage of PEG content. The 3D mesh samples were prepared in the format of a thin film with a series of graphene oxide weight percentages (100 wt %, 66.7 wt %, 50 wt %, 40 wt %, 33.3 wt %, 28.6 wt %). The Poisson ratio was 0.17 and each sample was analyzed using 18 indentations by tip to determine the tensility by Young's modulus. The load peak force was 500 μN and loading time was 60 seconds.

Manipulating Mechanical Properties of Mesh Complex Material

In order to adapt to the different micro-environmental requirements of tissue cells, the 3D scaffold should display sufficient flexibility and efficiently support various in vitro culture systems. Therefore, to manipulate the mechanical properties of the 3D mesh, PEG was added to the GO with the expectation that PEG could enhance tensile properties of the mixed material. PEGs are biocompatible materials that are an oligomer of ethylene oxide and available with several different molecular weights such as 400 Da, 1000 Da, 6000 Da and 8000 Da. PEG readily forms a hydrogel through the crosslinking of its hydroxyl groups to carboxyl groups of other compounds via stable hydrogen bonds. It is expected that this linking property allows the PEG oligomer to crosslink with GO to form a complex GO-PEG hydrogel.

To verify the PEG crosslinking effect, the inventors tested the Young's modulus and hardness of GO meshes with various percentages of PEG. A range of GO:PEG ratios were tested, while keeping the GO proportion constant, to determine the relationship between Young's modulus or hardness and different PEG percentages (FIGS. 2A and 2B). For ease of quantification by a nanoindentation device, a film of GO-PEG mixed materials was prepared. The thicknesses of the GO-PEG films tested were about 2 μm. As a control, a pure GO film without PEG was prepared. When the maximum constant load was 500 μN and load time was 60 seconds, the Young's modulus of the pure GO film was 15.83±2.55 GPa (FIG. 2A). Additionally, a series of GO-3D meshes with different ratios of GO:PEG were tested. With increasing PEG content, the Young's modulus and hardness gradually declined (FIGS. 2A and 2B), reflecting the reduced hardness of the structure. When the GO-3D mesh contained 71.4% PEG, the Young's modulus was 5.75±1.05 GPa which is a 3-fold reduction relative to 100% GO content. Therefore, the introduction of PEG into the GO-3D mesh makes the mesh more flexible. Since PEG has excellent biocompatibility and no bio-toxicity, these GO-3D meshes had sufficient structural flexibility to be compatible for in vitro applications. For all remaining analyses, 66.7% of the PEG 6000 Da was chosen for generating the GO-3D mesh. These analyses represent non-limiting examples. It will be understood by one of ordinary skill in the art that the percentage and molecular weight of PEG can be varied. Preferably, the molecular weight of PEG is between 6000 Da and 8000 Da. The lower molecular weight PEG is a liquid, whereas the higher molecular weight PEG (e.g., 6000 Da and 8000 Da) is a solid.

Imaging the 3D Mesh Using Scanning Electron Microscopy (SEM)

A scanning electron microscope (SEM SU8000, Hitachi, Tokyo, Japan) with Quartz PCI software (version 5) was used to analyze and image the surface and cross-section of a GO-3D mesh and the cells cultured within it. An accelerating voltage of 10 kV and a current of 5 mA were applied during the imaging and analysis process. The samples were spattered with platinum to enhance surface conductivity prior to imaging. The cross section of GO-3D mesh was prepared by cutting the mesh in half to obtain the interior cross section view. The 3D mesh with the cells was prepared by fixation in 2.5% glutaraldehyde in pH 7.4 phosphate buffer solution (PBS) for 15 minutes at room temperature. Then, the mesh was washed two times with PBS buffer and distilled water. Afterwards, the dehydration process was performed with graded concentrations of ethanol of 50%, 60%, 70%, 80%, 90%, and 99%. Post-dehydration, the samples were heated at 65° C. overnight. The PCI software was utilized to analyze the pore size with data from 500 pores calculated for each sample. In addition, the pore diameter of a subset of representative samples were quantified using a calibrated scale on the SEM images and Image Pro Plus 6.0 Software (Media Cybernetics, Rockville, Md.).

Porosity and Swelling Test for the GO-3D Mesh

Figure 3:
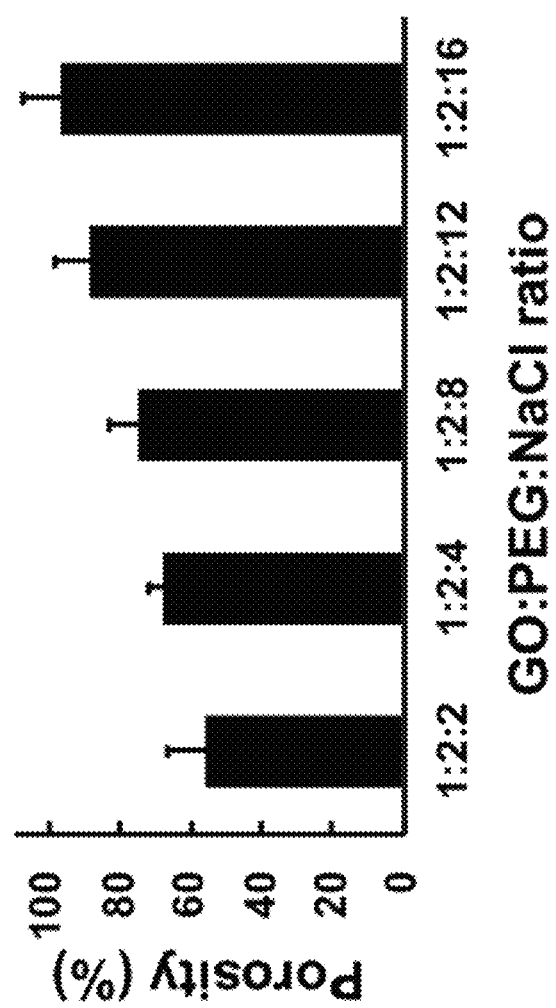
FIG. 3 is a graph illustrating porosity for various GO-3D meshes.

The porosity of the 3D mesh was measured by the liquid displacement method with ethanol as the displacement liquid based on its strong penetration ability. After heating at 65° C. overnight, the dry weights of the mesh ($W_d$) were immediately measured using an electronic balance (OHAUS Corp., Pine Brook, N.J.). Afterwards, the 3D mesh was immersed in ethanol for 5 minutes and the wet weights ($W_w$) were quantified. The porosity was calculated by the following formula: porosity=$(W_w-W_d)/(\rho \times \pi \times (D/2)^2)$ where "$W_w$" and "$W_d$" are the wet and dry weights, respectively, of the scaffold, "$\rho$" is the density of ethanol (0.789 g/cm$^3$), "$\pi$" is the discrete value of pi (3.14), "D" is the diameter of the scaffold, and "H" is the height of the scaffold as described. FIG. 3 shows the mean±standard deviation for four replicates of each mesh type with the experiment repeated two times with two different sets of preparations. The swelling ratio of the 3D mesh was obtained by immersing the dry mesh in a PBS solution maintained at 37° C., comparable to the temperature conditions associated with a standard cell culture incubator. Two separate assessments were conducted with four different mesh preparations each on two different time courses. The mesh was weighed in a short-term series to determine the wet weights ($W_{wPBS}$) upon initial exposure to aqueous solution through four hours with the $W_{wPBS}$ determined by placing the wet scaffold onto filter paper to remove excess fluid and then weighing the wet material following the procedure of Unnithan et al., "Nanoengineered bioactive 3D composite scaffold: A unique combination of graphene oxide and nanotopography for tissue engineering applications," *Composites Part B* 2016, 90 503-511. The swelling percentage of the mesh was calculated by the formula: swelling %=[($W_{wPBS}$−$W_d$)/$W_d$]×100% where "$W_d$" is the dry weight of the scaffold with the wet weight ($W_{wPBS}$) determined at each time point. FIGS. 4A and 4B show the mean±the standard deviation for four replicate samples of each mesh type. A separate set of assessments was conducted to determine the long term swelling properties with the terminal point at 3 weeks (FIG. 4B) after the initial immersion and the swelling percentage determined as previously described.

Tailoring Porosity of the 3D Mesh Based on NaCl Crystalline Forms

One of the major challenges associated with biocompatible 3D scaffolds is tailoring the porosity and pore size distribution to ensure efficient mass transfer, sufficient oxygen and nutrient transfer and penetration, and sufficient interior space for cells in culture. Varying pore sizes within a mesh may provide a reservoir for nutrients and oxygen for cultured cells; however, metabolic wastes may also be entrapped in micropores and affect the survival, differentiation, or proliferation of the cells. Therefore, the pore size, porosity, and pore interconnectivity of GO-3D meshes were analyzed and optimized for cells grown in a 3D matrix. Furthermore, depending on the cell type or application, the porosity and pore interconnectivity can be optimized accordingly. To obtain flexible 3D mesh that can be utilized in multiple biological applications, GO-3D meshes with a series of porosities were fabricated by modulating the amount of NaCl added to the GO:PEG mixture. The amount of NaCl added affects the porosity and pore sizes of the 3D meshes, thereby contributing to the overall structural properties of the cellular scaffold.

A possible mechanism of formation of the GO-3D mesh in the presence of NaCl is described herein. A GO-3D mesh can be prepared by simple blending and heating of PEG and GO sheets in ethanol. After the GO-PEG mixture reaches homogeneity, the product forms a gel that is then combined with NaCl to promote formation of NaCl crystals within the gel. With the extensive exposure to elevated temperature (e.g., 80° C. for 24 hours), the ethanol evaporates leaving the GO:PEG gel with NaCl crystals integrated throughout. The NaCl is then washed away with copious distilled water rinses leaving the porous skeleton within the GO:PEG 3D structure.

Gel structures are commonly formed via chemically crosslinking and/or physical crosslinking methods. Hydrogen bond formation is one physical interaction used in preparation methods for physical gels (or hydrogels). In the theorized model of how the GO-3D mesh forms (shown in FIG. 1), the hydrogel forms through hydrogen bonds established between carboxyl groups of the GO sheets and the hydroxyl groups of the PEG polymer. The long and flexible PEG hydroxyl side chain could connect to GO by hydrogen bonds to form a spatial network structure. Alternatively, the PEG could interact with epoxy bridges and other functional groups present in the GO.

When mixing PEG and GO only, the resultant mesh could be porous. However, it would be difficult to tailor the porosity, pore size distribution features, and stability. Since the PEG 6000 has a high molecular weight and a long molecular structure, the hydrogen bonds between the PEG and the GO sheets are not strong enough to form and hold pores of sufficient size or stability to sustain a physical environment for cell growth. Therefore, the salt leaching method is used to incorporate a porous scaffold within the stable gel bond structure of the GO:PEG gel. The contributions of both PEG and NaCl have a synergistic effect to improve and stabilize the 3D structure based on the flexible properties of GO. By adding NaCl to the GO:PEG, the NaCl establishes a crystalline shape in the GO:PEG mixture when it transitions from liquid to gel solid. The size and the number of the NaCl crystals can be controlled by changing the ratio of NaCl to GO and PEG. The pores are revealed as the crystals are removed with distilled water washing. With increasing NaCl concentration, there is a corresponding increase in the porosity of the GO-3D mesh. Therefore, the amount of NaCl can be changed to modulate porosity of the resulting GO-3D mesh.

A GO-3D matrix with 66.7% PEG content was prepared, by mixing 7.5 mg GO and 15 mg PEG 6000. Different amounts of NaCl were then introduced into the mixture. The resultant ratios of GO:NaCl were 1:2, 1:4, 1:8, 1:12, and 1:16, respectively (shown in FIG. 3, panel A). When the ratio of GO to NaCl was lower than 1:12 or porosity was over 90%, the 3D mesh tended to be fragile because there are numerous large pores within the mesh structure. With increasing porosity, there is a corresponding reduction in structural density and network structure complexity of the 3D mesh based on the displacement approach used to quantify porosity. The inventors determined that a porosity less than 90% provides sufficient interior pores and pore connectivity to be stable and still flexible enough to be utilized in cell culture applications. Previous studies by others have suggested that a porosity range from 60% to 90% can be used for tissue engineering using different polymers and substrates.

A GO-3D mesh with 75% porosity was used to test the swelling ratio, determine stability over time, image the GO-3D mesh structure (surface and interior), and determine the biocompatibility of the mesh with two types of cells.

Swelling Capacity of the 3D Mesh

The swelling capacity of a 3D mesh is important for biological applications so that the material can be compatible with the aqueous microenvironment of cells. This aspect of traditional graphene-polymer scaffolds has been a challenge with regard to the synthetic methods that resulted in material that was too brittle or was insufficiently able to absorb and retain aqueous solutions. In order to determine whether the disclosed GO-3D mesh was suitable for biological applications, the inventors conducted a swelling test on the GO-3D mesh (FIG. 4A) and quantified the swelling response to PBS over a short time frame (4 hours). The GO-3D meshes were immersed in PBS solution maintained at 37° C. (pH 7.4). The values shown in FIG. 4A are the average and standard deviation of four measurements (n=4). The 3D mesh generated by the method disclosed herein had rapid and stable swelling properties. The swelling percentage reached peak within 10 minutes and remained stable for the duration of the assay. Moreover, the material had outstanding swelling capacity as the GO-3D mesh absorbed a solution weight seven times more than the 3D mesh itself (based on dry weight measurements). There was no statistical difference in swelling or stability over the period of the assay. In order to determine whether or not the swelling properties were stable over longer time frames, a second assessment over 3 weeks was conducted (FIG. 4B). Welling measurements were measured daily for five days, followed by interval steps through a three-week window. There was no statistical difference in swelling or stability over the period of the assay. These results demonstrated the feasibility of cell culture application with the GO-3D mesh since biocompatible nanomaterials would need to be able to absorb fluids sufficiently well to mimic the aqueous cellular microenvironment. In addition, the soft, wet surface and cellular affinity can greatly reduce the irritation to surrounding tissues in applications associated with tissue engineering.

Morphological Study of GO-3D Mesh

Figure 5:
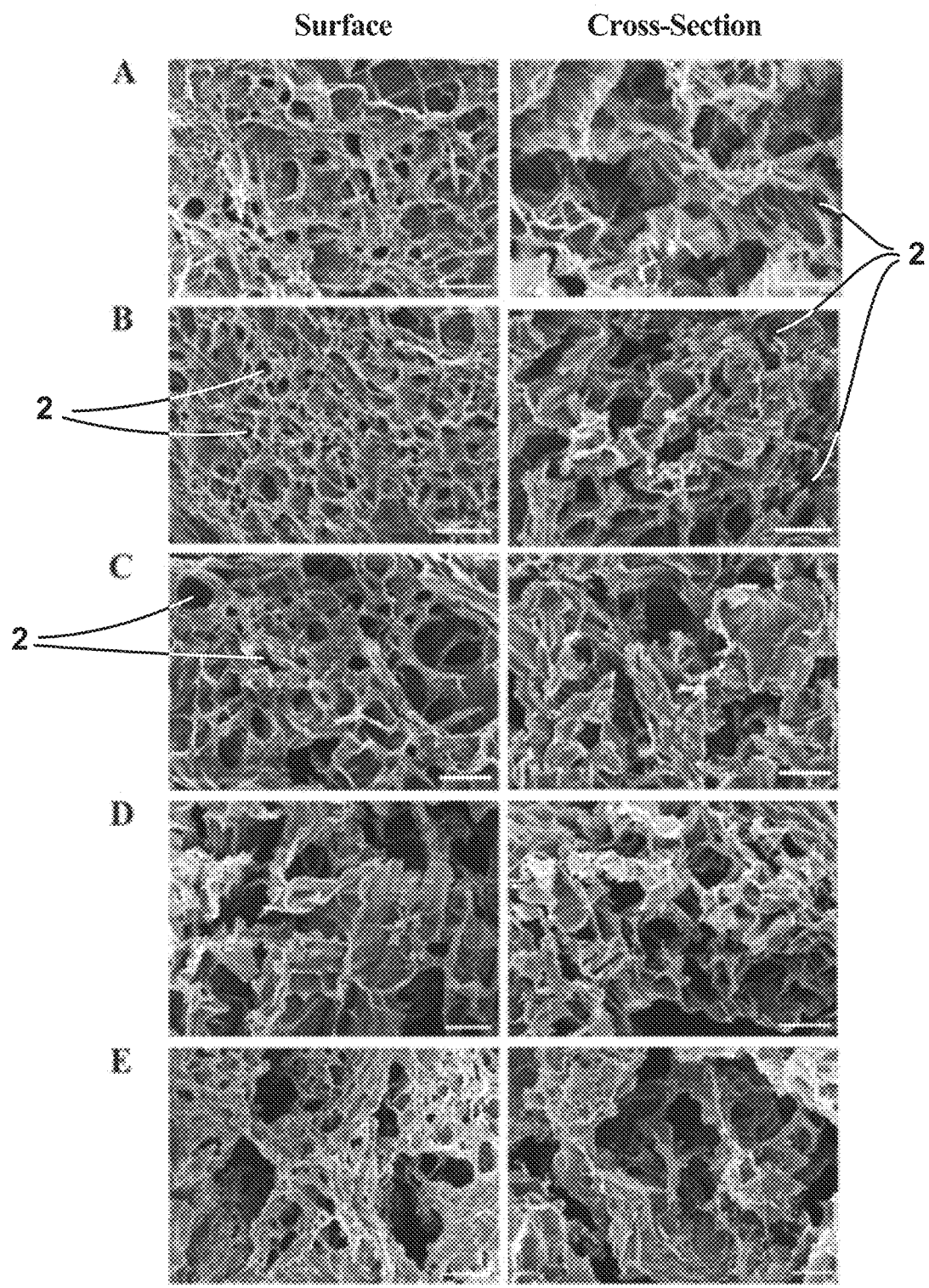
FIG. 5 includes panels of scanning electron microscope (SEM) images of the surface and interior cross sections of various GO-3D meshes.

Scanning electron microscopy (SEM) was used to analyze the 3D mesh surface and inner interconnectivity structure. SEM imaging was conducted on GO-3D mesh with different ratios of GO:PEG to NaCl. Samples were fixed with glutaraldehyde and sputtered with platinum to enhance surface conductivity prior to imaging. The acceleration voltage (10 kV) and the current (5 mA) were applied consistently during the imaging and analysis process. The cross sections of GO-3D mesh were obtained by cutting the mesh in half to reveal the interior cross section view. Results demonstrated that the 3D mesh was clearly formed with extensive porosity having pores 2 (shown in FIG. 5). Pore size was estimated by SEM images, with the average pore size ranging from about 5 μm to about 20 μm. Changing the ratio of NaCl in the GO-PEG mixture altered the sample porosity of the GO-3D mesh. FIG. 5, panels A-D, shows the surface structure and cross section SEM images of representative GO-3D mesh samples prepared with different amounts of NaCl. The average pore diameter and standard deviation were quantified for a representative sample from each of the ratios with the number of measured pores indicated for each: 1:2:2 (10.14±3.03; n=35 pores) (FIG. 5, panel A); 1:2:4 (7.34±2.67; n=80 pores) (FIG. 5, panel B); 1:2:8 (12.83±5.22; n=80 pores) (FIG. 5, panel C); 1:2:10 (18.79±5.17; n=80 pores) (not shown); 1:2:12 (30.62±6.80; n=80 pores) (FIG. 5, panel D); and 1:2:16 (31.31±8.57; n=80 pores) (FIG. 5, panel E). The average pore size increased with increasing NaCl content. Therefore, a balance of GO-3D mesh porosity less than 90% with a ratio of NaCl higher than 1:12 (GO:NaCl) provides a stable structure with regular porosity. When the porosity was less than 90%, as the ratio of NaCl increased, the number of pores increased with good interconnectivity. Cross-section comparison revealed that the interior pores in the mesh were larger and more interconnected with a higher NaCl concentration. The pores inside the 3D mesh ranged from about 5 μm to about 30 μm in diameter. However, when the porosity was over 90% (Compare FIG. 5, panels D and E), the high ratio of NaCl induced NaCl aggregates that resulted in irregularly-shaped pores with reduced interconnectivity. Therefore, it was noted that a balance of GO-3D mesh porosity less than 90% with a ratio of NaCl higher than 1:12 (GO:NaCl) provides a stable structure with regular porosity. Previous studies investigating 3D scaffolds in tissue engineering have suggested that varying scaffold pore size can impact different cellular functions with micropore sizes (<10 μm) improving the cell proliferation and macropore sizes (>50 μm) promoting the migration, interaction and differentiation of a variety of cell types. The porosity and pore interconnectedness of the GO-3D mesh disclosed herein is, therefore, within this range and supports the applicability to cell culture systems.

Vascular Cell Culture

Primary cultures of mouse brain derived vascular endothelial cells and mouse brain derived vascular fibroblast cells were obtained from CD1 adult mouse brain (Cell Biologics, Chicago, Ill.) and maintained in complete Dulbecco's Modification of Eagle's Medium with Glutamax and 4.5 g/L glucose (Gibco BRL, Grand Island, N.Y.) supplemented with 10% fetal bovine serum, penicillin solution (100 U/ml), and streptomycin (100 μg/ml). The vascular endothelial cells and the perivascular fibroblasts were plated at a density of 2500 and 5000 cells/well on gelatin-coated (Gelatin-based coating 0.2% solution, Cell Biologics) 4-well plates in complete DMEM medium. Cells were used through passage 4 and the specific culture times for each experiment are indicated in the FIG. legends. Cell counts for assay plating were determined by counting a diluted suspension with an EVE automated cell counter (NanoEn Tek, Waltham, Mass.); specific plating densities are indicated in the legends.

Fluorescence Imaging

The cells were cultured in a four-well-plate for 24 hours, respectively, during which time the nanoparticles incorporated into the cells. The two types of labeled cells were trypsinized and transferred to a GO-3D mesh for 7 days. The cells in the 3D mesh were fixed with 3.7% paraformaldehyde in PBS and washed in PBS with 0.1% Triton X 100 and 1 μm TO-PRO-3 iodide (642/661) to label the nuclei. The 3D mesh was cryosectioned at 10 μm thickness for confocal imaging of the silica nanoparticle labeled cells in the mesh (Zeiss LSM 510 META confocal system, UND SMHS Image Analysis Core).

Cell Proliferation

Cell proliferation was assessed by the MTT assay according to the manufacturer's instructions (Vybrant® MTT Cell Proliferation Assay Kit, ThermoFisher) with minor modifications to accommodate the GO-3D mesh. The cells were also seeded on gelatin-coated plastic as a control group for comparison. Mouse brain vascular-derived endothelial cells and fibroblast cells were seeded at a density of $2.5 \times 10^3$ and $5 \times 10^3$ respectively in parallel cultures (5 replicates each) on GO-3D mesh and plastic in 48-well tissue culture plates and cultured for 3, 5 and 7 days. The GO-3D meshes were first washed with DMEM medium to fully saturate the mesh prior to coating it with gelatin (0.2% solution, Cell Biologics) for 30-45 minutes at RT, based on manufacturer's recommendations and our experience with the coating solution. The two types of cells were incubated in 37° C. with 5% $CO_2$ atmosphere, with standard humidity control (Nu-Aire, Plymouth, Minn.). The proliferation was determined following standard manufacturer's protocols for the MTT Assay (Invitrogen, ThermoFisher, US) with 10 μL MTT added per well and incubated at 37° C. In the case where the inventors wanted to assay the GO-3D mesh cells and the plastic adherent cells from within the same plated well, the mesh was moved to a new well prior to completing the assay. After 4 h, 100 μL of sodium-dodecyl-sulfide (SDS)/HCl solution (Invitrogen) was added into each well. The absorbances were measured at 570 nm using a microplate reader (BioTek, Winooski, USA). Values were collected for the plastic (control), the cells on GO-3D mesh, and the cells that were in the same well as the mesh, but not adhered to the mesh (referred to as "plastic-adherent" population). The mean and standard deviation for replicate values were assessed by two-way ANOVA with culture condition and time in culture as the primary variables in the analysis. Sidak's adjustment for multiple comparisons was used for all paired-wise comparisons (JMP version 10; SAS Institute Software and Prism GraphPad, GraphPad Prism Software, San Diego, Calif.); results were graphed using Prism GraphPad and composites generated in Adobe Photoshop (CS6, Version 13, Adobe Systems Incorporated, San Jose, Calif.).

Vascular Cell Immunolabeling and Imaging In Vivo and In Vitro

In vivo immunolabeling. The brain-derived blood vessels were imaged from embryonic day 11.5 mouse forebrain. The tissue was collected under an IACUC approved protocol and fixed in phosphate-buffered saline (PBS) solution with 4% paraformaldehyde. The tissue was then equilibrated to 30% sucrose solution and cryosectioned at 10 μm intervals using a Leica HM550 cryostat. The sections were blocked and permeabilized in 3% donkey serum (Vector Laboratories, Burlingame, Calif.), 0.1% Triton X-100, 1% bovine serum albumin (BSA) in PBS for 1 hour (h) at RT. The antibody incubation was 2 hours at RT. The sections were immuno-labeled to detect perivascular fibroblasts using NG2 proteoglycan polyclonal antibody (Abcam, Cambridge, Mass.) and *G. simplicifolia* lectin conjugated to fluorescein isothiocyanate (lectin-FITC, 1:200 dilution; Vector Labs, Burlingame, Calif.) to label the vascular endothelial cells. The nuclei were labeled with DAPI and the images collected with an Olympus BX51 equipped with three channel fluorescence using a 40× objective (1.4 numerical aperture). The images were post-processed with Photoshop to generate composites with scales indicated in the FIG. legends.

In vitro immunolabeling. The brain vascular-derived perivascular fibroblasts and endothelial cells were cultured solo or together in GO-3D mesh for 9 days and were then fixed in 4% paraformaldehyde-PBS. The GO-3D mesh was cryosectioned at 10 μm thickness and sections were blocked and permeabilized as above and the antibody incubation was 2 hours at RT. The antibodies used were: smooth muscle actin conjugated to Cy3 (1:2000 dilution, Sigma Immunochemicals, St. Louis, Mo.) to label brain-derived perivascular (fibroblast) cells and *G. simplicifolia* lectin conjugated to FITC (1:200 dilution; Vector Labs, Burlingame, Calif.) to label the endothelial cells. Nuclei were labeled with To-Pro3 iodide (Molecular Probes, Eugene, Oreg.). Antibody dilutions were made in block solution as described above. Slides were permanently mounted with Vectashield mounting medium (Vector Labs). For acquiring images, alpha Plan-Fluar 63×/1.4 numerical aperture or 100×/1.45 numerical aperture oil objective lenses were used on a Zeiss LSM 510-Meta confocal microscope equipped with Zen-Software (Zeiss, Germany). The confocal pin hole was adjusted to 1 Airy Unit (AU) and z-series stacks were collected with 4 average passes in 1 μm intervals at a 1024×1024 resolution. The 2D images, the 3D Z-stack images, and orthogonal projections were processed using the Zen-Software (Zeiss, Germany) and post-processed to generate composites using Photoshop.

RNA Isolation, cDNA Synthesis, and PCR

Total RNA was extracted from endothelial and fibroblast cells cultured on plastic, GO-3D mesh, and any cells that adhered to the plastic surrounding the GO-3D mesh (plastic-adherent). The Arcturus® PicoPur® RNA Isolation Kit (Applied Biosystems) was used to isolate and purify the RNA. The RNase-free DNase kit was used as an on-column DNase I digestion (Qiagen, 3 Kunitz units per column isolation). RNA was extracted from cells cultured on plastic using 100 μl extraction buffer applied directly to the cell culture well. GO-3D mesh was placed in 1.5 ml tubes, then submerged in 100 μl extraction buffer. After the mesh was removed from the well, the remaining plastic-bound cells were extracted with 1000 extraction buffer and processed as a separate sample for comparison (plastic-adherent). Total RNA was quantified using the Nanodrop DS-11 Spectrophotometer (DeNovix Wilmington, Del.), and sample quality ensured with A260/280 ratios between 1.8 and 2.0. The cDNA was generated via reverse transcription of 150-200 ng of total RNA using the GeneAmp RNA PCR Core Kit (Applied Biosystems). Total RNA was incubated with Murine Leukemia Virus (MuLV)-derived Reverse Transcriptase (50 U/μl), RNase Inhibitor (20 U/μl), PCR Buffer II (500 mM KCL and 100 mM Tris-HCl), $MgCl_2$ (25 mM), Random Hexamers (50 μM), Oligo d(T) (50 μM), dATP (100 μM), dTTP (100 μM), dGTP (100 μM), dCTP (100 μM), and nuclease-free water in a C1000 Touch Thermal Cycler (BioRad Laboratories, Hercules, Calif.) at 42° C. for 15 minutes followed by 5 minutes at 99° C. For the PCR amplification, 1-2 μl of cDNA were combined with 0.25 μm forward and reverse primers, up to 10 μl with Platinum PCR Supermix (Invitrogen) and amplified using standard PCR cycling: 95° C., 5 min [(95° C., 1 min; 53-58° C., 30 sec; 72° C., 1 min×30); 4° C., ∞]. Primer sequences and amplicon sizes are provided in Table 2 (below).

Biocompatibility Evaluation of a GO-3D Mesh

Figure 6:
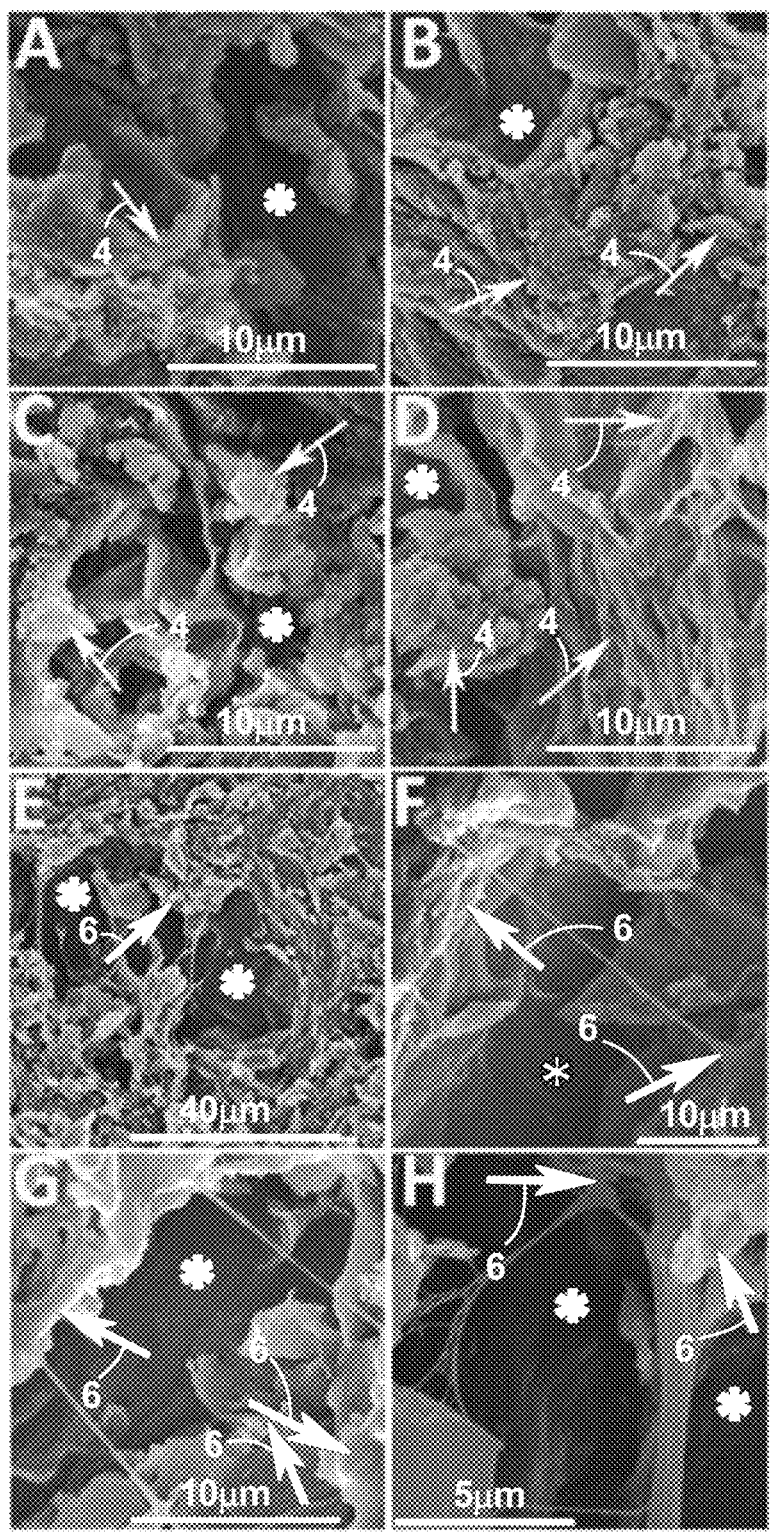
FIG. 6 includes panels of scanning electron microscope (SEM) images showing cell cultures on GO-3D meshes.

In order to determine the biocompatibility of a GO-3D mesh, a cell culture application for the GO-3D mesh was tested using brain-derived vascular endothelial cells 4 (FIG. 6, panels A-D) and fibroblasts 6 (FIG. 6, panels E-H), respectively. Heterotypic vascular cell populations were tested with the mesh for two reasons: (1) the use of heterotypic populations more closely reflects the heterogeneity and complexity of an in vivo system and (2) vascularization of any engineered tissue is required for tissue stability and successful incorporation. The cells were trypsinized and then transferred to two GO-3D meshes and allowed to colonize the mesh over the course of 3-5 days in solo or direct contacting coculture. These tests demonstrated that the GO-3D mesh can be used to establish microenvironment conditions that support heterotypic (or monotypic) cell-cell interactions in vitro.

Primary cultures of embryonic mouse endothelial cells 4 and fibroblast cells 6 were grown on 3D meshes for 7 days and then SEM images were taken to visualize the cell density and morphology on the GO-3D meshes. As shown in FIGS. 6A-6H, the SEM results illustrate that these two types of cells were cultured on the GO-3D mesh, effectively adhered to the 3D mesh, and divided and survived over time.

The GO-3D mesh made of GO and PEG 6000 with a ratio GO:PEG of 1:2 and porosity of 75% was utilized to evaluate the biocompatibility. Endothelial cells 4 and fibroblast cells 6 were trypsinized and transferred to non-tissue culture wells with pieces of the GO-3D mesh coated with gelatin and 3D mesh, respectively. SEM images indicated that the two types of cells grew and proliferated well on GO-3D mesh after incubating 7 days, and the 3D mesh surface was embedded by multiple layers of cells. Both cell types 4, 6 firmly adhered to the 3D mesh surface and the porous scaffold network inside. Qualitative views of some regions of the GO-3D mesh culture showed the endothelial and fibroblast cells 4, 6 on the interior pores of GO-3D mesh. The endothelial cells 4 grown in solo culture (FIG. 6, panels A-D) form tightly associated layers that cover the interior of the GO-3D mesh. The cells line the interior pores and layer across the intercalated regions between pores. The perivascular fibroblasts 6 have a distinct morphology reflecting the highly migratory behavior often displayed by this cell type. The perivascular fibroblasts 6 adhere to the mesh and inside the pores and send cell projections across distances, often with extensive fiber formation (FIG., panels E-H). Regions of graphene are indicated by asterisks for comparison.

A flexible, porous, biocompatible GO-3D mesh was generated. For cell culture application of 3D mesh, the 3D mesh would not only support survival of sensitive endothelial and fibroblast cells, but would also allow formation of a complex network of processes adhering to the GO-3D mesh structure (surface and interior). To determine whether the endothelial and fibroblast cells interacted in the GO-3D microenvironment, FITC and Ru(BPY) doped fluorescent silica nanoparticles were utilized to label endothelial cells and fibroblast cells for confocal visualization of cell-cell interactions in the 3D mesh.

Figure 7:
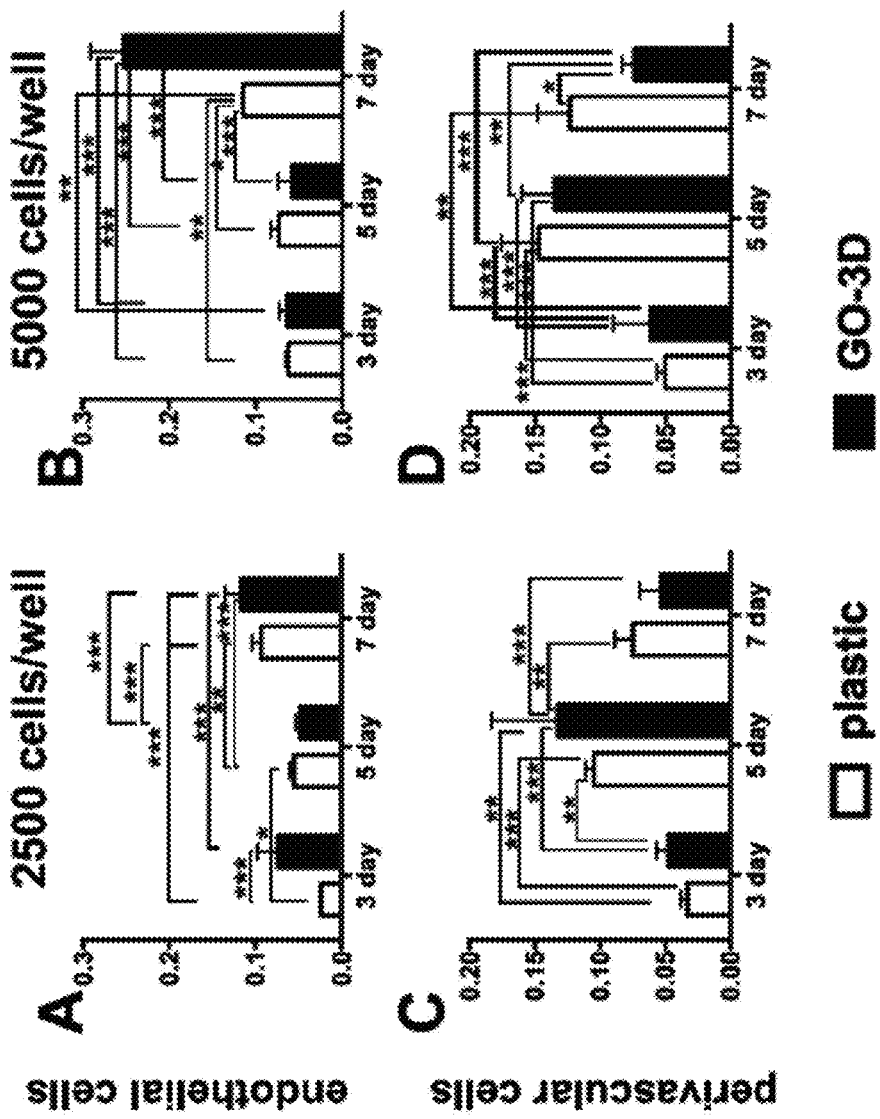
FIG. 7 includes graphs comparing cell proliferation of cell cultures on plastic versus GO-3D mesh.
Figure 8:
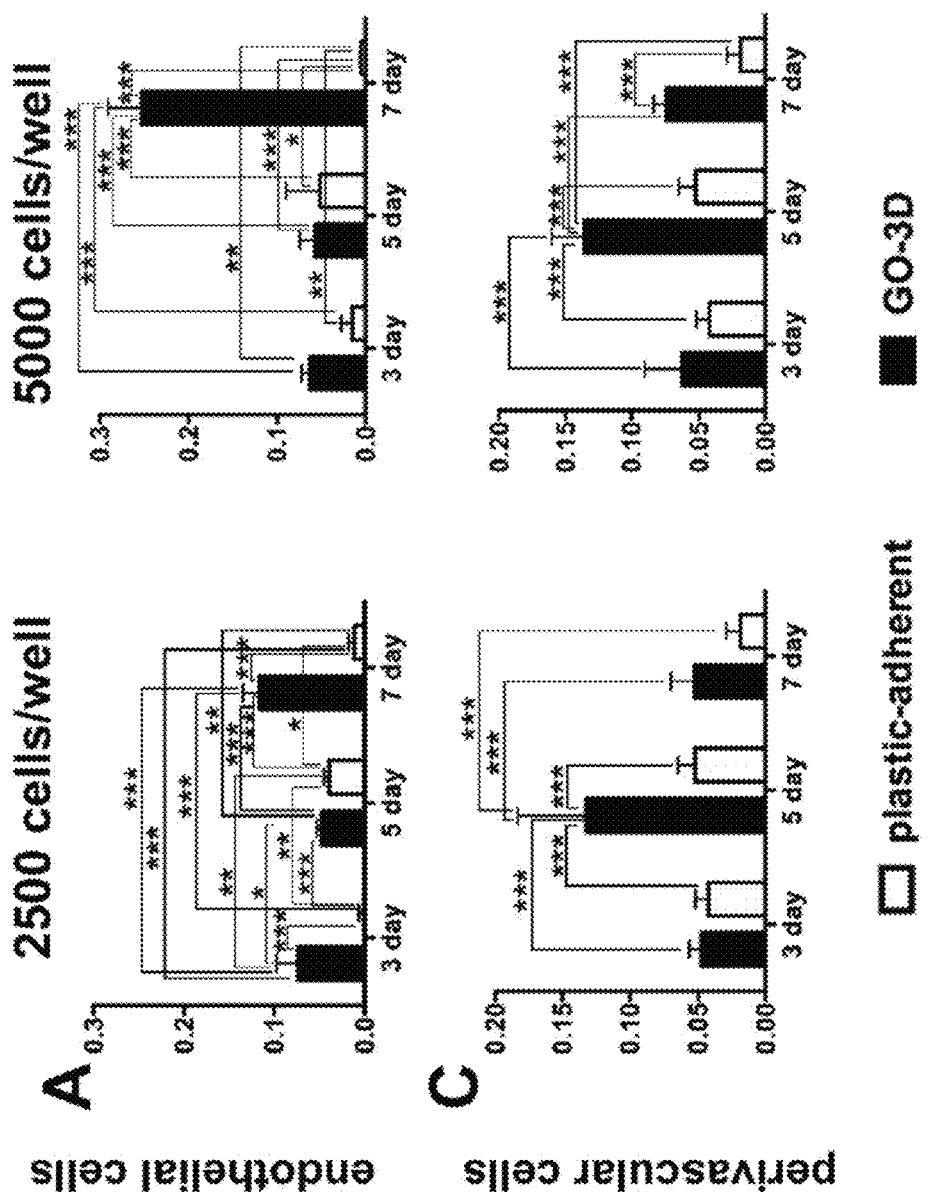
FIG. 8 includes graphs comparing GO-3D and plastic-adherent cell populations.

In order to quantify vascular cell proliferation on the GO-3D mesh, an MTT assay was conducted on both cell types to determine population effects over time and to compare the responses of the two cell types on the mesh. Cells were plated on standard tissue culture plastic wells and, in parallel, on GO-3D mesh in plastic wells. This constituted three conditions: (1) baseline growth on plastic, (2) growth on GO-3D mesh, and (3) residual cell growth on the plastic in the GO-3D mesh well for cells not adhering to the mesh (plastic-adherent). Two sets of analyses were conducted comparing growth on 2D plastic versus GO-3D (FIG. 7) and the difference in population distribution between the cells in the same well, but adhered to the GO-3D mesh versus the residual cells in the well (FIG. 8). Two initial plating densities and three time points were compared for each cell type using two-way ANOVA and the statistical results for growth condition, time in culture, and the interaction of the two variables are presented in Table 1.

| Interaction (Condition X Time) (Dfn = 1, Dfd = 24) | Growth Condition (Dfn = 1, Dfd = 24) | Time in Culture (Dfn = 2, Dfd = 24) |
|---|---|---|
| I. Comparison: Plastic versus GO-3D ||| 
| EC2500  12.85%, F = 11.61, p = 0.003 | 11.7%, F = 21.15, p = 0.0001 | 62.15%, F = 56.13, p < 0.0001 |
| EC5000  23.53%, F = 55.87, p < 0.0001 | 8.49%, F = 40.3, p < 0.0001 | 62.93%, F = 144.44, p < 0.0001 |
| Fb2500  6.73%, F = 3.09, p = 0.0638 | 0.71%, F = 0.65, p = 0.4269 | 66.47%, F = 30.57, p < 0.0001 |
| Fb5000  8.53%, F = 4.72, p = 0.0186 | 3.75%, F = 4.15, p = 0.0528 | 66.04%, F = 36.57, p < 0.0001 |
| II. Comparison: Plastic-adherent (same well) versus GO-3D |||
| EC2500  24.71%, F = 35.41, p < 0.0001 | 59.33%, F = 170.04, p < 0.0001 | 7.59%, F = 10.88, p = 0.0004 |
| EC5000  38.07%, F = 55.87, p < 0.0001 | 34.61%, F = 132.49, p < 0.0001 | 21.05%, F = 40.29, p < 0.0001 |
| Fb2500  14.06%, F = 6.54, p = 0.0054 | 23.61%, F = 21.96, p < 0.0001 | 36.54%, F = 17.00, p < 0.0001 |
| Fb5000  10.89%, F = 8.26, p = 0.0019 | 44.26%, F = 67.10, p < 0.0001 | 29.02%, F = 22.00, p < 0.0001 |

The endothelial cells cultured on GO-3D mesh had higher values in the MTT assay relative to the cells grown on plastic alone (FIG. 8, panels A and B). This difference was particularly apparent at the higher plating density. A different growth pattern was observed in the perivascular fibroblasts that had initial improved growth on the GO-3D mesh relative to the 2D plastic at 3 and 5 days in culture (FIG. 8, panels C and D). However, the cells showed reduced values in the MTT assay by 7 days in culture for both growth substrates with the most pronounced negative effect observed on the GO-3D mesh. In comparing the assessment of cells within the same well (plastic-adherent versus GO-3D) it was clear that the two cell types showed distinct distribution and growth patterns. The endothelial cells were largely restricted to the GO-3D mesh with minimal residual cells detected on the plastic in the same well (FIG. 8, panels A and B) with no major differences observed with initial plating density. In contrast, the perivascular fibroblasts grew well on both the 2D plastic and the GO-3D, although the MTT assay values from GO-3D mesh were consistently larger, compared to the plastic-adherent population at the 3 and 5 day time points, regardless of initial plating density (FIG. 8, panels C and D).

Figure 9:
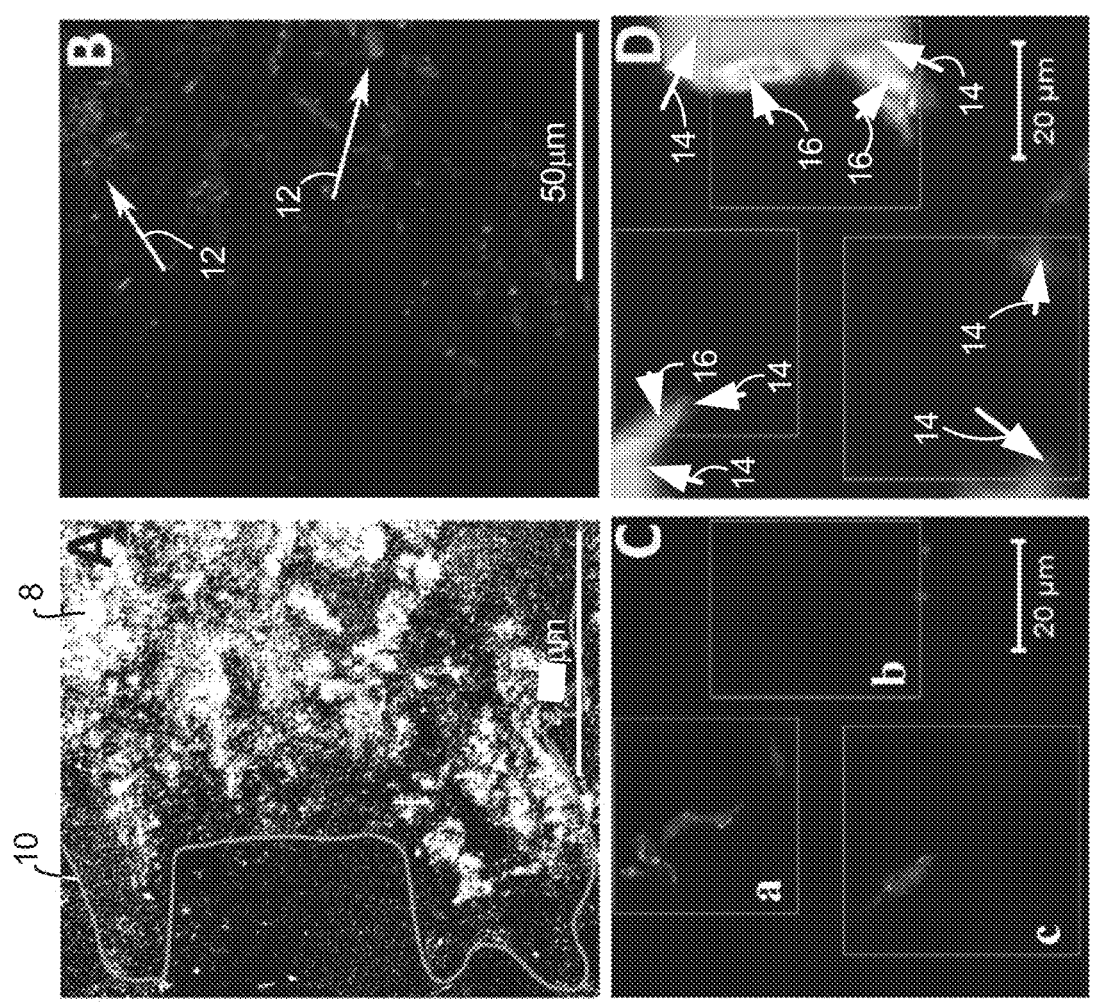
FIG. 9 includes images comparing RNA isolation from cells cultured on plastic versus GO-3D mesh.

As part of the GO-3D mesh biocompatibility assessment, it was important to determine whether or not gene expression studies could be conducted on cells grown on the mesh; specifically, whether or not the system was amenable to RNA isolation. This is a critical requirement for any 3D scaffold material since gene expression changes could then be linked to single or multi-cell type culture parameters. The vascular-derived endothelial cells and perivascular fibroblast cells were cultured separately on plastic and on GO-3D mesh. RNA was isolated from both populations (FIG. 9) as well as the plastic-adherent population derived from the well containing the GO-3D mesh. Expression of targeting two different reference genes (18S and Gapdh) and vascular cell markers (PdgfβR and Akap12/Gravin) was detected in the treatment conditions and the specific primers and amplicon sizes are provided in Table 2.

TABLE 2

Primer Sequences and amplicon sizes for PCR

| Gene Name | SEQ ID NO | Forward/Reverse Primers (Mouse) | Amplicon Size |
|---|---|---|---|
| 18S | 1 | (F) 5'-GACACGGACAGGATTGACAGATTGATAG-3' | 129 bp |
|  | 2 | (R) 5'-GTTAGCATGCCAGAGTCTCGTTCGTT-3' |  |
| Gapdh | 3 | (F) 5'-GTGGCAAAGTGGAGATGGTTGCC-3' | 288 bp |
|  | 4 | (R) 5'-GATGATGACCCGTTTGGCTCC-3' |  |
| Pdgfβ | 5 | (F) 5'-GTGGCAAAGTGGAGATGGTTGCC-3' | 173 bp |
|  | 6 | (R) 5'-GGCTTCTTTCGCACAATCTCA-3' |  |
| Akap12/ Gravin | 7 | (F) 5'-CCGAGAAGAGAAAGGAGCAA-3' | 147 bp |
|  | 8 | (R) 5-AAGGCAACTCCACCTTCTCA-3' |  |

Figure 10:
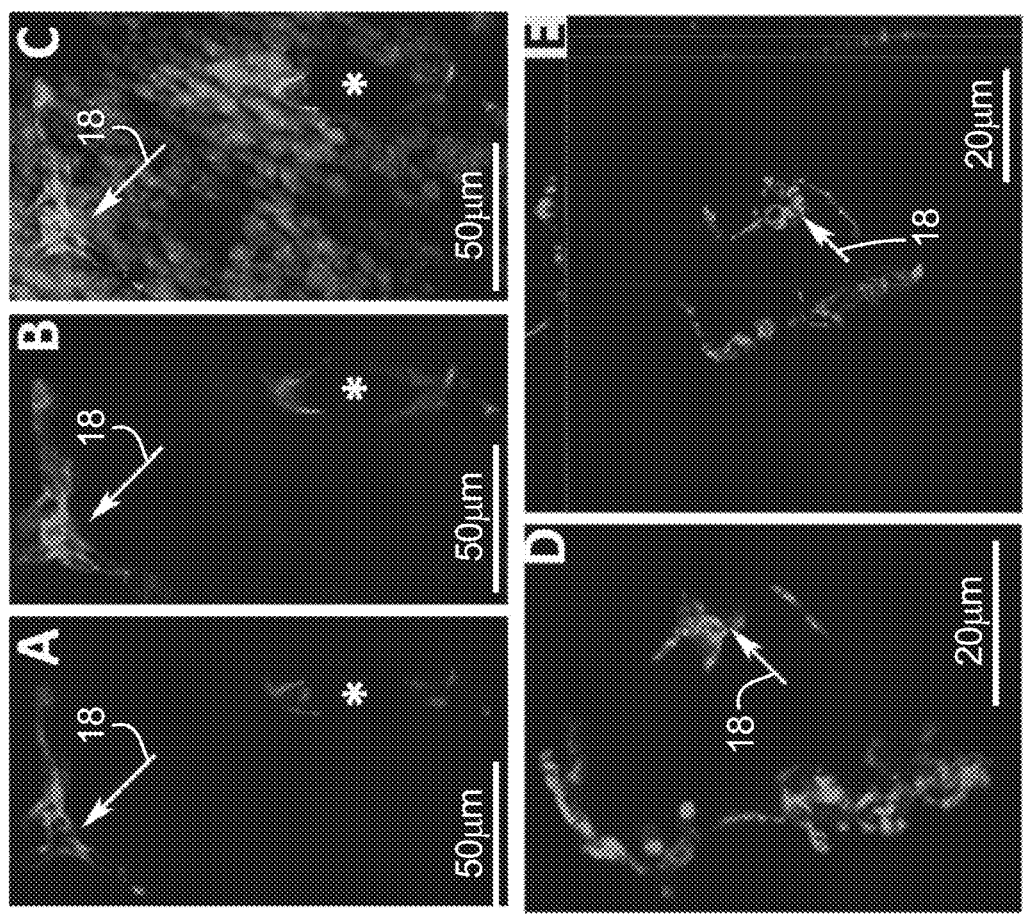
FIG. 10 includes panels of confocal microscopy of collagen labeling on GO-3D mesh and differentially labeled endothelial and perivascular cells, respectively.

As an additional assessment of biocompatibility, it was important to characterize the vascular cells grown together on the GO-3D mesh since these two cell types are closely associated in blood vessels in vivo. GO-3D mesh was coated with gelatin and then vascular-derived endothelial and fibroblast cells were grown in heterotypic direct coculture for 7 days. GO-3D mesh was fixed and cryosectioned at 10 μm intervals. A representative section is shown that was threshold inverted to depict the graphene 8 with line 10 marking the edge of the section (FIG. 10, panel A). The section was immunolabeled for collagen (FIG. 10, panel B) to identify areas of protein coating on the mesh. The arrows 12 point to areas of concentrated collagen deposition, although the protein is present throughout the section shown. The vascular cell-GO-3D mesh sections were also labeled for cell-type specific markers (FIG. 10, panel C) and confocal fluorescence Z-stack images generated of the endothelial cells (isolectin G4), perivascular fibroblasts (smooth muscle α-actin), and nuclei (ToPro3) (not labeled). Bright field imaging of the fluorescence Z-stack series is shown for comparison (FIG. 10, panel D). The arrows 14 indicate the zones with pores inside the GO-3D mesh, and the arrows 16 indicate the cells growing in the GO-3D mesh.

Since the GO-3D mesh is coated with gelatin prior to cell plating, the distribution of collagen Type IV was immunolabeled across cryosections of the mesh, revealing a punctate pattern of labeling (FIG. 10, panels A and B). The endothelial cells and perivascular fibroblasts were in close apposition to one another in the mesh, often localized to the edges of the mesh or on the interiors of the pores. A bright field image of the GO-3D mesh with cells is shown (FIG. 10, panel D) with open areas (no mesh scaffold, bright zone) in which the cells adhered to the edge of the mesh.

Figure 11:
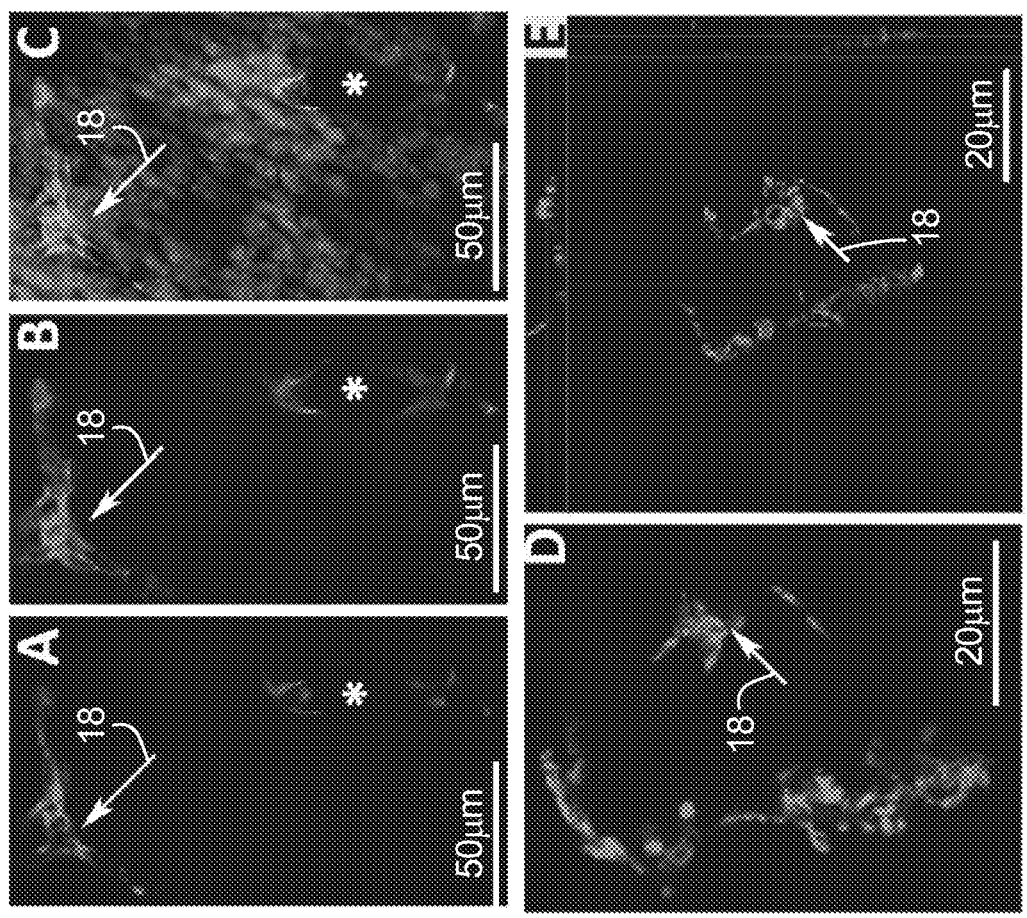
FIG. 11 includes panels of standard fluorescence microscopy images of the two types of vascular cells in a developing cortical blood vessel as well as confocal imaging of endothelial and perivascular cells on GO-3D mesh.

In a normal blood vessel, the endothelial cells form the lumen of the vessel and the perivascular fibroblasts are positioned ablumenally, as seen for blood vessels in embryonic mouse forebrain shown in saggital and cross-section view (FIG. 11, panels A-C). To provide a comparison of vessels in vivo, embryonic day 11.5 mouse forebrain was fixed, cryosectioned at 10 µm intervals and labeled for cell-type specific markers. Endothelial cells were labeled with isolectin G4 (FIG. 11, panel A) and perivascular fibroblasts were labeled for NG2 proteoglycan as a pericyte marker (FIG. 11, panel B). The overlay of the two channels with nuclei localized with DAPI (FIG. 11, panel C) is shown for comparison. The arrows 18 indicate a saggital view of a branched capillary blood vessel and the asterisks indicate the lumen of a larger vessel in cross-section. Confocal imaging of the vascular cells grown together on GO-3D mesh revealed morphological features akin to those of vessels in vivo, with the two distinct cell populations not only closely associated, but forming cords reminiscent of capillaries. The orthogonal views of the z-series confocal stack in the GO-3D mesh revealed that the cells were closely intertwined on the mesh pores (FIG. 11, panel E), reflecting the suitability of the 3D microenvironment as a growth scaffold for these distinct vascular populations.

A novel, simple, easily reproducible and low cost synthetic method for GO-3D mesh is described herein. One valuable feature of the GO-3D mesh is that the porosity and tensility of the scaffold is tunable based on the component ratios and synthesis used. PEG plays a role for effectively adjusting the mechanical properties of the 3D mesh and adapting the final structure for a range of in vitro applications. The addition of the salt leaching method to the synthesis approach synergizes well with the GO:PEG ratio synthetic process and allows the tailoring of the porosity and pore size distribution of the GO-3D mesh. Finally, endothelial cells and fibroblast cells were successfully cultured using the developed GO-3D mesh. These results demonstrate the potential of the GO-3D mesh described herein to be used in cell culture applications.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of making a porous three-dimensional graphene mesh, the method comprising:
   combining graphene oxide (GO) and poly(ethylene)(glycol) (PEG) in an alcohol solvent to form a mixture;
   adding a selected amount of sodium chloride (NaCl) to the mixture, wherein the amount of NaCl added to the mixture is selected to generate a ratio of GO to NaCl of 1:12 or greater and a porosity of a resulting gel of less than 90%;
   heating the mixture to form the resulting gel; and
   washing the resulting gel with water to remove the NaCl from the resulting leaving behind a three-dimensional graphene scaffold mesh having stable pores.

2. The method of claim 1, wherein the GO comprises a dispersion of GO in ethanol.

3. The method of claim 1, wherein the mixture is heated to a temperature between about 60° C. and about 85° C. for between about 1 hour and about 36 hours to form the resulting gel.

4. The method of claim 1, further comprising:
   drying the resulting gel at a temperature between about 40° C. and about 70° C. for between about 1 hour and about 24 hours.

5. The method of claim 1, wherein the scaffold mesh has a porosity between about 50% and about 90%.

6. The method of claim 1, wherein the Go and the PEG are combined at a GO:PEG weight ratio between 1:1 and 1:3.12.

7. The method of claim 1, wherein an average pore size of the scaffold mesh is between about 5 μm and about 50 μm.

8. The method of claim 1, wherein the alcohol solvent is methanol, ethanol, propanol, butanol, or pentanol.

* * * * *

UNITED STATES PATENT AND TRADEMARK OFFICE
CERTIFICATE OF CORRECTION

PATENT NO. : 10,988,732 B2
APPLICATION NO. : 16/774921
DATED : April 27, 2021
INVENTOR(S) : Ying Zhang, Julia Xiaojun Zhao and Diane Darland Page 1 of 1

It is certified that error appears in the above-identified patent and that said Letters Patent is hereby corrected as shown below:

In the Specification

After Column 1, Line 10 Insert:
-- STATEMENT OF Government Support
This invention was made with Government support under 4P20GM104360-04 (UND0021237) awarded by the National Institutes of Health and under CHE 0947043 (UND0021724) awarded by the National Science Foundation. The Government has certain rights in the invention. --

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*